(12) United States Patent
Rozental et al.

(10) Patent No.: US 11,419,503 B2
(45) Date of Patent: Aug. 23, 2022

(54) ULTRASOUND DETECTION BY OPTICAL PASSIVE-DEMODULATION INTERFEROMETRY USING PHOTONIC INTEGRATED CIRCUITS (PIC)

(71) Applicant: TECHNION RESEARCH & DEVELOPMENT FOUNDATION LTD., Haifa (IL)

(72) Inventors: Amir Rozental, Haifa (IL); Yoav Hazan, Haifa (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 218 days.

(21) Appl. No.: 16/639,598

(22) PCT Filed: Sep. 3, 2018

(86) PCT No.: PCT/IB2018/056704
§ 371 (c)(1),
(2) Date: Feb. 17, 2020

(87) PCT Pub. No.: WO2019/049016
PCT Pub. Date: Mar. 14, 2019

(65) Prior Publication Data
US 2020/0196874 A1 Jun. 25, 2020

Related U.S. Application Data

(60) Provisional application No. 62/555,066, filed on Sep. 7, 2017.

(51) Int. Cl.
*A61B 8/00* (2006.01)
*A61B 5/00* (2006.01)
(Continued)

(52) U.S. Cl.
CPC .............. *A61B 5/0097* (2013.01); *A61B 8/00* (2013.01); *G01H 9/004* (2013.01); *G02F 1/11* (2013.01)

(58) Field of Classification Search
CPC ..... A61B 5/0097; G01S 15/8968; G02B 6/00; G02F 1/33; H04N 5/225; G06T 7/0012; G06T 7/0014; G06T 7/0016
See application file for complete search history.

(56) References Cited

U.S. PATENT DOCUMENTS

2014/0114187 A1 4/2014 Rozental et al.
2014/0376001 A1 12/2014 Swanson
(Continued)

OTHER PUBLICATIONS

Wang., "Multiscale photoacoustic microscopy and computed tomography," Nature Photonics, vol. 3, No. 9, pp. 503-509, Sep. 2009.
(Continued)

*Primary Examiner* — Rochelle D Turchen
(74) *Attorney, Agent, or Firm* — Kligler & Associates Patent Attorneys Ltd

(57) ABSTRACT

An apparatus for optical detection of ultrasound includes one or more optical resonators (OR—200), one or more optical passive-demodulation interferometers (OPDI—22), and one or more respective electro-optical readout circuits (EORC—24). The one or more optical resonators (OR) are configured to modulate respective carrier frequencies of optical signals indicative of US waves impinging thereon. The one or more OPDI are implemented in one or more photonic integrated circuits (PIC), wherein each OPDI is configured to demodulate the optical signal output by the respective OR, so as to generate a respective intensity-modulated optical signal. Each OPDI includes an interferometer (32) having imbalanced arms (323, 325) that are recombined using an optical hybrid (34). The one or more respective EORC are each configured to measure the inten-
(Continued)

sity demodulated optical signal produced by the respective OPDI, and to output a respective electrical signal.

18 Claims, 5 Drawing Sheets

(51) Int. Cl.
    *G01H 9/00* (2006.01)
    *G02F 1/11* (2006.01)

(56) References Cited

U.S. PATENT DOCUMENTS

2016/0178680 A1\* 6/2016 Ntziachristos ..... G01R 29/0878 73/643
2018/0028117 A1 2/2018 Desjardins et al.

OTHER PUBLICATIONS

Taruttis et al., "Advances in real-time multispectral optoacoustic imaging and its applications," Nature Photonics, vol. 9, No. 4, pp. 219-227, Apr. 2015.
Razansky et al., "Near-field radiofrequency thermoacoustic tomography with impulse excitation," Medical Physics, vol. 37, No. 9, pp. 4602-4607, Sep. 2010.
Kellnberger et al., "Magnetoacoustic Sensing of Magnetic Nanoparticles," Physical Review Letters, vol. 116, No. 10, pp. 108103-1 through 108103-6, Mar. 11, 2016.
Sethuraman et al., "Spectroscopic intravascular photoacoustic imaging to differentiate atherosclerotic plaques," Optics Express, vol. 16, No. 5, pp. 3362-3367, Mar. 2008.
Jansen et al., "Intravascular photoacoustic imaging of human coronary atherosclerosis," Optics Letters, vol. 36, No. 5, pp. 597-599, Mar. 2011.
Ling et al., "High-sensitivity and wide-directivity ultrasound detection using high Q polymer microring resonators," Applied Physics Letters, vol. 98, No. 20, p. 204103-1 through 204103-3, May 2011.
Rosenthal et al., "High-sensitivity compact ultrasonic detector based on a pi-phase-shifted fiber Bragg grating," Optics Letters, vol. 36, No. 10, pp. 1833-1835, May 15, 2011.
Chao et al., "High-frequency ultrasound sensors using polymer microring resonators," IEEE transactions on ultrasonics, ferroelectrics, and frequency control, vol. 54, No. 5, pp. 957-965, May 2007.
Zhang et al., "Backward-mode multiwavelength photoacoustic scanner using a planar Fabry-Perot polymer ultrasound sensor for high-resolution three-dimensional imaging of biological tissues," Applied Optics, vol. 47, No. 4, pp. 561-577, Feb. 1, 2008.
Rosenthal et al., "Wideband Fiber-Interferometer Stabilization With Variable Phase", IEEE Photonics Technology Letters, vol. 24, No. 17, pp. 1499-1501, Sep. 1, 2012.
Tadayon et al., "Polymer waveguide Fabry-Perot resonator for high-frequency ultrasound detection", IEEE Transactions on Ultrasonics Ferroelectrics and Frequency Control, vol. 61, No. 12, pp. 2132-2138, Dec. 2014.
Li et al., "A transparent broadband ultrasonic detector based on an optical micro-ring resonator for photoacoustic microscopy", Scientific Reports, vol. 4, pp. 1-8, Mar. 2014.
Rosenthal et al., "Sensitive interferometric detection of ultrasound for minimally invasive clinical imaging applications," Laser Photonics Review, vol. 8, No. 3, pp. 450-457, May 2014.
Rosenthal et al., "Wideband optical sensing using pulse interferometry," Optics Express, vol. 20, No. 17, pp. 19016-19029, Aug. 2012.
Nasu et al., "Temperature insensitive and ultra wideband silica-based dual polarization optical hybrid for coherent receiver with highly symmetrical interferometer design," Optics Express, vol. 19, No. 26, pages B112-B118, Dec. 2011.

Rosenthal et al., "Spatial characterization of the response of a silica optical fiber to wideband ultrasound," Optics Letters, vol. 37, No. 15, pp. 3174-3176, Aug. 1, 2012.
Veres et al., "Characterization of the spatio-temporal response of optical fiber sensors to incident spherical waves," The Journal of the Acoustical Society of America, vol. 135, No. 4, pp. 1853-1862, Apr. 2014.
Wang et al., "Tip-sensitive all-silica fiber-optic Fabry-Perot ultrasonic hydrophone for charactering high intensity focused ultrasound fields," Applied Physics Letters, vol. 103, No. 4, pp. 044102-01 though 044102-5, Jul. 22, 2013.
Jotzu et al., "Continuous phase stabilization and active interferometer control using two modes," Journal of Modern Optics, vol. 59, No. 1, pp. 42-45, Jan. 2012.
Huntley et al., "Temporal phase-unwrapping algorithm for automated interferogram analysis", Applied Opticas, vol. 32, No. 17, pp. 3047-3052, Jun. 10, 1993.
Hazan et al., "Passive-demodulation pulse interferometry for ultrasound detection with a high dynamic range," Optics Letters, vol. 43, No. 5, pp. 1039-1042, Mar. 1, 2018.
Zimmermann et al., "C-Band Optical 90-degree-Hybrids Based on Silicon-on-Insulator 4X4 Waveguide Couplers," IEEE Photonics Technology Letters, vol. 21, No. 3, pp. 143-145, Feb. 2009.
International Application #PCT/IB2018/056704 search report dated Dec. 26, 2018.
Rose, "Ultrasonic Guided Waves In Solid Media", pp. 1-174, Cambridge University Press, 2014.
Wang et al., "Photoacoustic Tomography: In Vivo Imaging from Organelles to Organs," Science, issue 335, pp. 1458-1462, Mar. 23, 2012.
Olivares et al., "Sputtered SiO2 as low acoustic impedance material for Bragg mirror fabrication in BAW resonators," IEEE Transactions on Ultrasonics, Ferroelectrics, and Frequency Control, vol. 57, No. 1, pp. 23-29, Jan. 2010.
Gabai et al., "Multiplexing of fiber-optic ultrasound sensors via swept frequency interferometry," Optics Express, vol. 23, No. 15, pp. 1-10, Jul. 27, 2015.
Liang et al., "Fiber-Laser-Based Ultrasound Sensor for Photoacoustic Imaging," Scientific Reports, No. 7, pp. 1-10, Jan. 10, 2017.
Xia et al., "An optimized ultrasound detector for photoacoustic breast tomography," Medical Physics, vol. 40, No. 3, pp. 032901-1 through 032901, Mar. 2013.
Winkler et al., "Noise-equivalent sensitivity of photoacoustics," Journal of Biomedical Optics, volum 18, No. 9, pp. 097003-1 through 097003-10, Sep. 2013.
Tadayon et al., "Optical micromachined ultrasound transducers (OMUT)—a new approach for high-frequency transducers", IEEE Transactions on Ultrasonics, Ferroelectrics, and Frequency Control, vol. 60, No. 9, pp. 2021-2030, Sep. 2013.
O'Brien et al., "A sensitive optical micro-machined ultrasound sensor (OMUS) based on a silicon photonic ring resonator on an acoustical membrane," Scientific Reports, issue 5, pp. 1-9, Sep. 22, 2015.
Beard et al., "Transduction mechanisms of the Fabry-Perot polymer film sensing concept for wideband ultrasound detection", IEEE transactions on ultrasonics, ferroelectrics, and frequency control, vol. 46. No. 6, pp. 1575-1582, Nov. 1999.
Gallego et al., "High-sensitivity ultrasound interferometric single-mode polymer optical fiber sensors for biomedical applications," Optics Letters, vol. 34, No. 12, pp. 34, 1807-1807, Jun. 15, 2009.
Rosenthal et al., "Embedded ultrasound sensor in a silicon-on-insulator photonic platform," Applied Physics Letters Issue 104, pp. 021116-1 though 021116-4, year 2014.
Huang, "The influence of light propagation direction on the stress-induced polarization dependence of silicon waveguides," IEEE Photonics Technology Letters, vol. 18, No. 12, pp. 1314-1316, Jun. 15, 2006.
EP Application #18853563.7 Search Report dated Apr. 26, 2021.
Cobbold, "Foundations of Biomedical Ultrasound", Oxford University Press, pp. 1-4, year 2007.
De Brabander et al., "Integrated optical interferometer with micromechanical diaphragm for pressure sensing", IEEE Photonics Technology Letters, vol. 6, issue 5, pp. 671-673, May 1994.

(56) References Cited

OTHER PUBLICATIONS

Snyder et al., "Packaging Process for Grating-Coupled Silicon Photonic Waveguides Using Angle-Polished Fibers," IEEE Transactions on Components, Packaging and Manufacturing Technology, vol. 3, issue 6, pp. 954-959, Jan. 22, 2013.

Kellnberger et al., "Near-field thermoacoustic tomography of small animals", Physics in Medicine and Biology, vol. 56, No. 11, pp. 3433-3444, May 16, 2011.

* cited by examiner

ULTRASOUND DETECTION BY OPTICAL PASSIVE-DEMODULATION INTERFEROMETRY USING PHOTONIC INTEGRATED CIRCUITS (PIC)

CROSS-REFERENCE TO RELATED APPLICATIONS

This application is U.S. National Phase of PCT Application PCT/IB2018/056704, which claims the benefit of U.S. Provisional Patent Application 62/555,066, filed Sep. 7, 2017. The disclosure of these related applications are incorporated herein by reference.

FIELD OF THE INVENTION

The present invention relates generally to optical sensing, and particularly to methods and systems for the detection of ultrasound using optical passive interferometry that is implemented in photonic integrated circuits (PIC).

BACKGROUND OF THE INVENTION

Various schemes of optical interferometry may be used to manipulate and/or detect a physical signal. For example, in "Sensitive interferometric detection of ultrasound for minimally invasive clinical imaging applications," Laser Photonics, Rev. 8, No. 3, pages 450-457 (2014), Rosenthal et al. implement passive demodulation pulse interferometry in fiber optics, using a 3×3 fiber coupler and a phase-extraction algorithm. The authors introduce a coherence-restored pulse interferometry (CRPI) method for interferometric sensing, in which shot-noise limited sensitivity may be achieved alongside robust operation. CRPI is implemented with a fiber-based resonator, demonstrating over an order of magnitude higher sensitivity than that of conventional 15 MHz intravascular ultrasound probes. The performance of the optical detector is showcased in a miniaturized all-optical optoacoustic imaging catheter.

As another example, Hazan and Rosenthal describe a passive demodulation scheme for pulse interferometry, in "Passive-demodulation pulse interferometry for ultrasound detection with a high dynamic range," Optics Letters, Vol. 43, No. 5, pages 1039-1042, Mar. 1, 2018. The passive scheme is based on an unbalanced Mach-Zehnder interferometer and a 90° optical hybrid, which is implemented in a dual-polarization all-fiber setup. A passive scheme is demonstrated for detecting ultrasound bursts with pressure levels for which the response of conventional, active interferometric techniques became nonlinear.

Nasu et al. propose designs for a polarization beam splitter and an optical hybrid, in "Temperature insensitive and ultra-wideband silica-based dual polarization optical hybrid for coherent receiver with highly symmetrical interferometer design," OPTICS EXPRESS, Vol. 19, No. 26, pages B112-B118, December 2011. The proposed designs are based on highly symmetrical interferometers. The authors use retarders to implement 90-degree optical hybrids with balanced interferometers for phase demodulation in optical communication systems.

Jotzu et al. propose active phase stabilization of interferometers, in "Continuous phase stabilization and active interferometer control using two modes," Journal of Modern Optics, Volume 59, Issue 1, pages 42-54, 2012. The authors propose an approach to phase control capable of stabilization to an arbitrary phase setting by producing a linear error signal in the phase. The basic principle lies in utilizing two distinct optical modes passing through the interferometer with non-identical optical path length differences resulting in two phase offsets. The modes could consist of different transverse-spatial, temporal, frequency or polarization modes depending upon the nature of the experiment and noise involved.

In "C-Band Optical 90-degree-Hybrids Based on Silicon-on-Insulator 4×4 Waveguide Couplers," IEEE Photonics Technology Letters, vol. 21, no. 3, February 2009, Zimmermann et al. demonstrate 4×4 multimode interference (MMI) couplers in a silicon-on-insulator rib waveguide technology that enable compact integrated fully passive optical 90-degree-Hybrid devices with operation across the C-band.

Pulse interferometry was proposed by Rosenthal et al., in "Wideband optical sensing using pulse interferometry," OPTICS EXPRESS, Vol. 20, No. 17, August, 2012, pages 19016-19029. The authors demonstrate a method for wideband interrogation of optical sensors. The method is suggested as an alternative to conventional coherent (narrow linewidth) and incoherent (wideband) continuous-wave (CW) interrogation. The method is based on a pulse laser source whose bandwidth is significantly broader than the resonance width of the sensor and on interferometric demodulation. The authors further suggest that the use of a wideband coherent source opens new possibilities for interrogation methods with an advantageous combination of properties that cannot be found in conventional CW methods.

SUMMARY OF THE INVENTION

An embodiment of the present invention provides an apparatus for optical detection of ultrasound, including one or more optical resonators (OR), one or more optical passive-demodulation interferometers (OPDI), and one or more respective electro-optical readout circuits (EORC). The one or more optical resonators (OR) are configured to modulate respective carrier frequencies of optical signals indicative of US waves impinging thereon. The one or more OPDI are implemented in one or more photonic integrated circuits (PIC), wherein each OPDI is configured to demodulate the optical signal output by the respective OR, so as to generate a respective intensity-modulated optical signal. Each OPDI includes an interferometer having imbalanced arms that are recombined using an optical hybrid. The one or more respective EORC are each configured to measure the intensity demodulated optical signal produced by the respective OPDI, and to output a respective electrical signal.

In some embodiments, the one or more OR are implemented in the one or more PIC.

In some embodiments, the one or more EORC are implemented in the one or more PIC.

In an embodiment, each OPDI and respective EORC are implemented on a single substrate.

In another embodiment, one or more of the OR, and the corresponding OPDI, and respective EORC, are implemented on a single substrate.

In some embodiments, the apparatus further includes a processor, which is configured to derive, from respective electrical signals output by the one or more EORC, an output indicative of the impinging US wave.

In some embodiments, the optical signals include optical pulses.

In an embodiment, the one or more OR include $\pi$-phase shifted Bragg gratings.

In another embodiment, the optical hybrid includes a 90-degree optical hybrid.

In some embodiments, the interferometer is configured to generate a predefined optical phase shift between the imbalanced arms, at the carrier frequency.

There is additionally provided, in accordance with an embodiment of the present invention, a method for optically detecting ultrasound (US) waves. The method includes using one or more optical resonators (OR) for modulating respective carrier frequencies of optical signals indicative of US waves impinging thereon. The optical signals are demodulated using one or more optical passive-demodulation interferometers (OPDI) implemented in one or more photonic integrated circuits (PIC), wherein each of the OPDIs includes an interferometer having imbalanced arms that are recombined using an optical hybrid, so as to generate respective intensity-modulated optical signals. The intensity demodulated optical signals are measured and outputted as respective electrical signals, using one or more electro-optical readout circuitries (EORC).

The present invention will be more fully understood from the following detailed description of the embodiments thereof, taken together with the drawings in which:

DETAILED DESCRIPTION OF EMBODIMENTS

Overview

Figure 1:
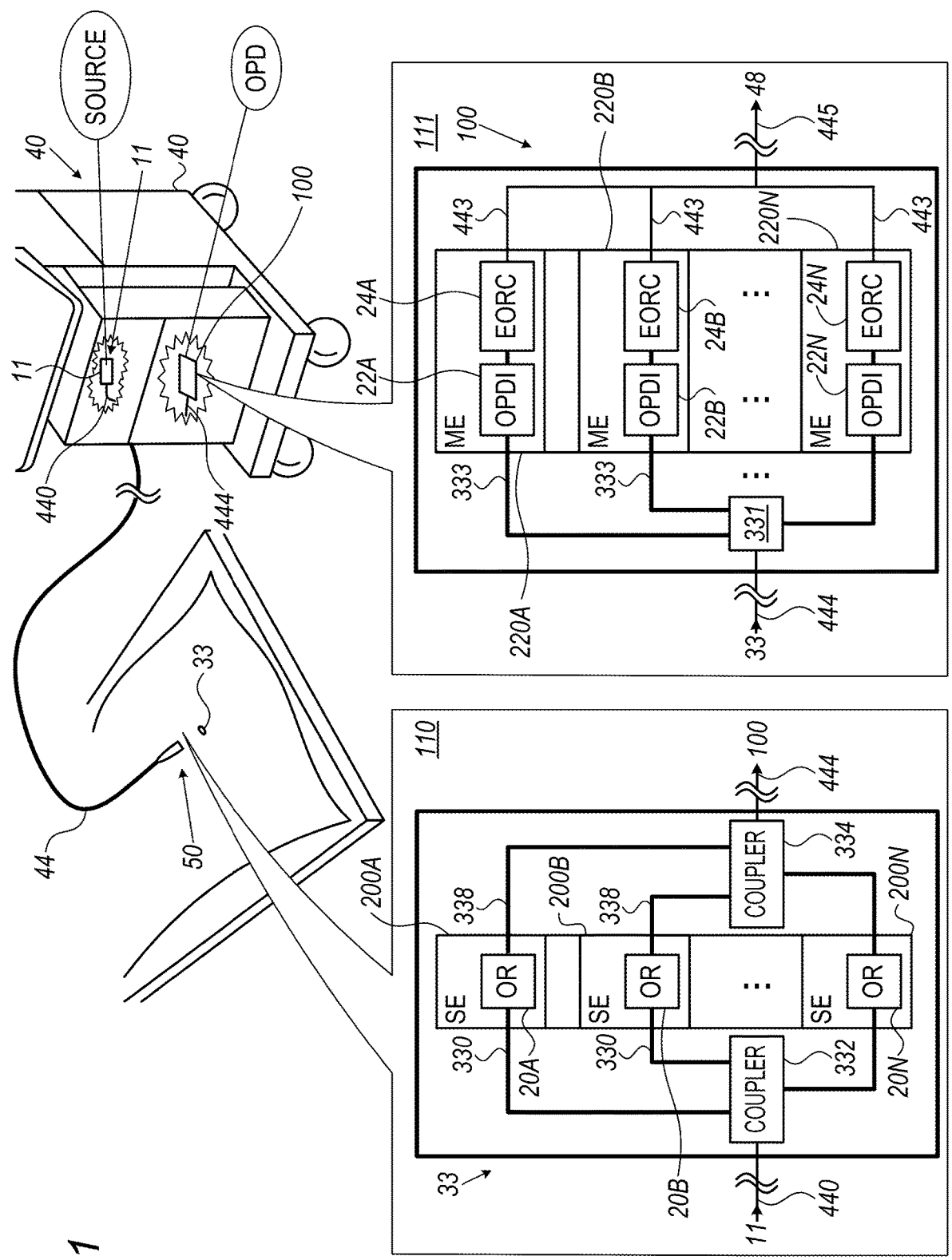
FIG. 1 is a block diagram that schematically illustrates an apparatus for optical detection of ultrasound, which is implemented in photonic integrated circuits (PIC), in accordance with an embodiment of the present invention.

Embodiments of the present invention that are described hereinafter provide apparatus and methods for the detection of ultrasound (US), which use optical passive-demodulation interferometry to optically detect US, implemented at least partially in photonic integrated circuits (PIC). US waves may result from various physical effects. One such effect is the thermoacoustic effect in which US waves are generated in a medium, such as human tissue, by electromagnetic radiation being absorbed by the tissue. The disclosed apparatus and methods can therefore be applied in various fields, such as, for example, in the field of minimally invasive medical diagnostics.

In some embodiments, a disclosed apparatus includes one or more optical resonators (OR), which may or may not be implemented in PIC, as described below, each OR is capable of optically sensing an impinging US wave. In some embodiments, each OR receives a train of optical pulses from a pulsed laser source. The OR is configured to modulate an optical carrier frequency of the optical pulses, in a way that the frequency modulation is indicative of an impinging US wave. The frequency modulated pulses are outputted, propagate, and coupled into an optically passive demodulation interferometer (OPDI), implemented in PIC, which is configured to demodulate the frequency-modulated optical pulse.

In an embodiment, the OPDI is implemented by a modified unbalanced Mach-Zehnder interferometer (MZI) that comprises an optical hybrid (i.e., an interferometer having imbalanced arms that are recombined using an optical hybrid). The OPDI outputs the intensity modulated pulses that to an electro-optical readout circuit (EORC), which measures the pulses to produce electric signals that are indicative of the impinging US wave. While the use of optical pulses is technically advantageous, the disclosed apparatus and method can be applied, with necessary changes, using a source whose bandwidth is larger than that of the OR, e.g., an amplified spontaneous emission source.

In the context of the present patent application and in the claims, the term "MZI" refers to an optical device used to determine the relative phase shift between two propagating guided wave optical pulses derived by splitting light from a single pulsed optical source. The term "unbalanced" means that the two arms of the MZI have different optical path lengths. The imbalance of the MZI enables the detection of time-dependent frequency shifts (i.e., frequency modulations) of the carrier frequency of the optical pulse inputs, which are proportional to a magnitude of a measured US wave.

In an embodiment, the OR, which is impinged upon by the US waves, comprises a π-phase shifted Bragg grating (π-BG), i.e., a Bragg grating with a narrow spectral transmission window in its bandgap created by a localized defect in the grating periodicity. The US waves modulate the center frequency of the π-BG, causing the filter to output a train of pulses having a modulated carrier frequency. The amount of frequency modulation is a good approximation of the linear function of the amplitude and timing of the US waves, and is thus directly indicative of those US waves. Alternatively, other types of OR can be used, and may be implemented in PIC, such as Fabry-Perot ORs or micro-ring resonators.

In some embodiments, the OPDI uses six out of m×n (m and n being integers) ports of a 90-degree optical hybrid that is connected to the outputs of an unbalanced MZI. In another embodiment, the 90-degree optical hybrid is realized by a 2×4 multimode interference (MMI) coupler, as described below. The unbalanced MZI is configured to generate an approximately 90-degree (i.e., 90 degrees with a possible deviation of several degrees) optical phase shift at the carrier frequency between the two optical paths of the MZI. The double 90-degree phase shifts, in tandem, lend themselves to large-scale implementation using planar PIC, as noted above and as further described below.

In other embodiments, the disclosed passive interferometry scheme is applied using multimode interference (MMI) couplers with optical hybrids that are not limited to a 90-degree shift. In some embodiments, the different optical paths of the unbalanced MZI induce a phase difference that is different from 90 degrees (i.e., a predefined optical phase shift between the two optical paths of the MZI, at the carrier frequency, that is different from 90 degrees). The unbalanced MZI output is coupled to an m×n MMI (m and n being integers) that acts as an optical hybrid. For example, in an embodiment, a 120-degree optical hybrid is implemented by a 3×3 MMI coupler.

In some embodiments, one or more arrays comprising at least part of the disclosed US optical sensing, conversion and measurement elements are fabricated as PIC on a single substrate or on different substrates. For example, in an embodiment, each OPDI and respective EORC are implemented in a PIC on a single substrate. As another example, in an embodiment, each OR, respective OPDI, and respective EORC are implemented in PIC on a single substrate. In alternative embodiments, OPDIs are implemented in a PIC, while ORs and/or EORC are implemented with other technologies, such as pigtailing the devices to optical fibers. In an embodiment, the OR and OPDI, but not the EORC, are implemented with PICS. The EORC is implemented, for example, using commercially available photodiodes.

Planar PIC designs may be implemented by numerous fabrication techniques for photonic integrated circuits, e.g., silicon photonics, glass waveguides, and polymer waveguides. In an embodiment, a use of multiple substrates, each disposed with a PIC, enables, for example, an US probe with an optical detection array having a curved geometry.

In some embodiments, the disclosed optical US detection method maintains a linear response at high acoustic pressure levels. Furthermore, the disclosed optical US detection method is compatible with AC-coupled electrical measurements, in which the electrical signals are high-passed before they are sampled. Thus, the dynamic range of the sampler circuit may be adjusted in correspondence with the magnitude of the US signals, while ignoring potentially larger low-frequency contributions to the signal.

In some embodiments, the OPDI outputs the frequency modulated pulses to the EORC, which, as noted above, is configured to convert the frequency-modulated optical pulse into an electrical signal. The EORC may or may not be implemented in PIC, as described below. A processor that receives the electrical signals is configured to derive from the electrical signals an output indicative of the US wave, such as to produce an ultrasound image (e.g., of an organ of a patient, probed with a minimally invasive medical diagnostic system).

The disclosed US imaging systems and methods can achieve both high sensitivity and high dynamic range, due to the disclosed OR that have an extremely low noise equivalent sound pressure, and the disclosed OPDI that converts the frequency modulated optical signals into intensity modulated signals, and the OPDI that measures the intensity modulated optical signals, at least part of implemented in PIC. The high sensitivity, which is more than an order of magnitude greater than that of a piezoelectric detection element of a same area, can enable, for example, high resolution US detection. An example application of the disclosed apparatus and method is an US imaging system that employs smaller-size detection elements in PICs so as to spatially resolve anatomical features that are unresolvable with current US imaging systems employing larger-size piezoelectric US detectors.

PIC-Based Apparatus for Ultrasound Detection

FIG. 1 is a block diagram that schematically illustrates an apparatus for optical detection of ultrasound, which is implemented in photonic integrated circuits (PIC), in accordance with an embodiment of the present invention. As seen, PIC-based array 33 seen in detail in inset 110, comprises sensing elements 200, each including an OR 20. PIC-based array 33 is implemented, by way of example, in a probe 50 of a minimally invasive medical diagnostic system.

PIC-based array 33 receives optical pulses from a pulsed source 11, via a fiber optic 440 which runs through cable 44. When impinged with US waves, PIC-based array 33 outputs frequency modulated pulses to a PIC-based OPDI array 100, via fiber 444 that is also included in cable 44.

In an embodiment, seen in inset 110, an optical coupler 332 couples the output of fiber optic 440 into a planar array of waveguides 330. Each waveguide 330 outputs the optical pulses to a respective optical sensing element 200 comprising OR 20 that frequency modulates the pulses. As seen in the embodiment, array 33 comprises multiple sensing elements 200A, 200B . . . 200N.

The frequency modulated pulses are outputted to an optical coupler 334 by OR 20 via a planar array of waveguides 338. Coupler 334 outputs the pulses to optical fiber 444. In an embodiment, seen in inset 110, an optical coupler 331 couples the output of fiber optic 444 into a planar array of waveguides 333. Each waveguide 333 outputs the optical pulses to a respective measurement element 220 that includes an OPDI 22. The frequency demodulated pulses are converted by OPDI 22 into light intensity modulated pulses. As seen, each measurement element 220 further comprises an electro-optical readout circuit (EORC) 24, which is configured to measure the intensity modulated optical pulses outputted by OPDI 22 circuit and output the resulting electrical signals to a processor 48 respective, via electrical leads 443 and electrical cable 445. In some embodiments, each OPDI 22 and the respective EORC 24 are implemented in a single PIC.

The block diagram shown in FIG. 1 is depicted purely by way of example. Any other suitable configuration can be used in alternative embodiments. For example, in some embodiments, OR 20, OPDI 22 and EORC 24 may be implemented in a single PIC located inside a probe, like inside a hand-held US probe. As another example, various optical elements in the disclosed apparatus can be implemented in fibers additionally or alternatively to the disclosed implementation in planar waveguides in a PIC.

For example, the EORC, which converts optical intensities into electrical signals, may be realized with an array of commercially available packaged photodiodes that are pigtailed to optical fibers. Similarly, the OR elements may be realized as in processing and packaging technologies different than as part of a PIC. For example, commercially available optical resonators may be assembled into an array 33.

US sensor array 33 is shown schematically as a single monolithic unit only for clarity of presentation. In practice, array 33 may be implemented by adjoining separate smaller sub-arrays. Such an implementation enables, for example, a curved geometry of electro-optical US sensing array 33.

Ultrasound Detection Using Optical Pulse Interferometry Passive-Demodulation

Figure 2:
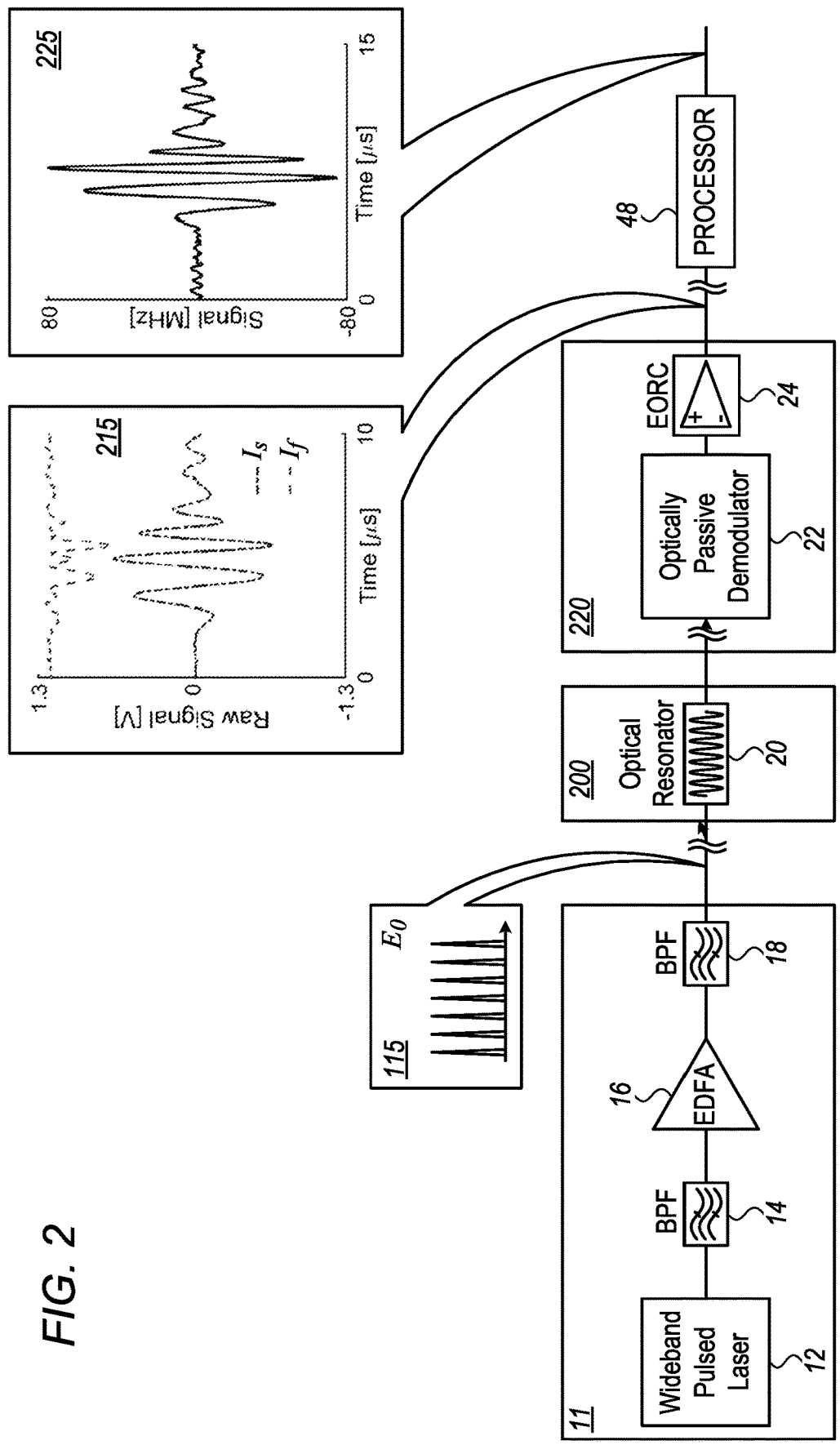
FIG. 2 is a block diagram that schematically illustrates details of the detection apparatus appearing in FIG. 1, in accordance with an embodiment of the present invention.

FIG. 2 is a block diagram that schematically illustrates details of the detection apparatus appearing in FIG. 1, in accordance with an embodiment of the present invention. As seen, optical pulse source 11 generates a train $E_0$ of filtered optical pulses, seen in inset 115. In an embodiment, source 11 comprises an infrared pulse laser 12 having a 1550 nm central wavelength (i.e., central frequency $v_0$ of 193.4 THz) with a pulse repetition rate of 250 MHz, pulse width of approximately 0.1 ps, and average power on the order of several tens of mW. The laser's output pulses are filtered down to a bandwidth of 0.4 nm around 1550 nm using a band-pass filter (BPF) 14, then amplified by an erbium-doped amplifier 16, and filtered by an additional 0.4 nm band-pass filter 18 to reject amplified spontaneous emission from the amplifier. In alternative embodiments, any other suitable numerical values may be used.

The train $E_0$ of filtered optical pulses is coupled to optical sensing element 200. As seen, sensing element 200 comprises an optical π-BG 20 that comprises an optical resonator that is highly sensitive to impinged ultrasound waves. In an embodiment, π-BG 20 has a resonance notch at a wavelength of 1550 nm, and a bandgap width of approximately 1 nm. Alternatively, any other suitable values may be used.

Figure 3:
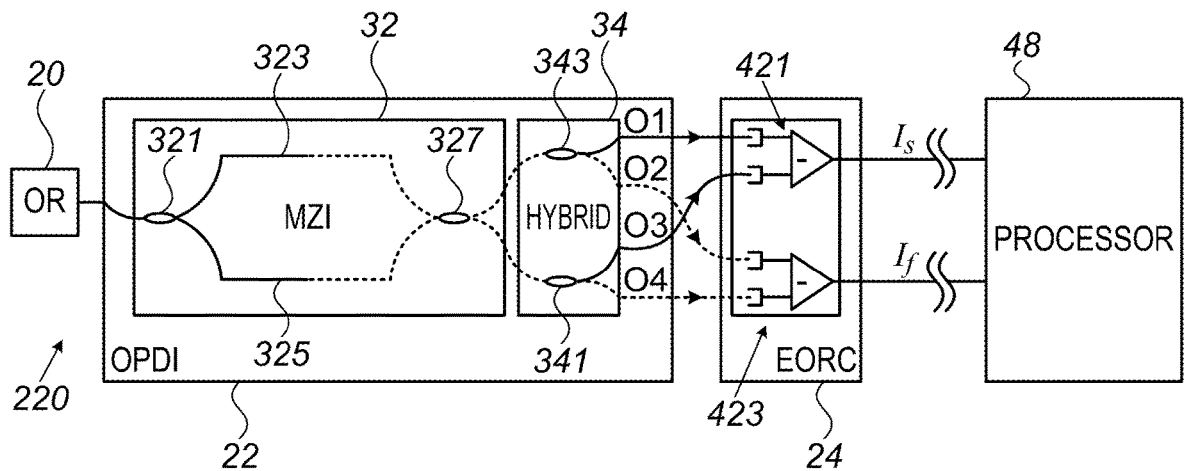
FIG. 3 is a block diagram that schematically illustrates details elements of the detection apparatus appearing in FIG. 2, in accordance with an embodiment of the present invention.

The output of π-BG 20 is coupled to OPDI 22, which is described in detail in FIG. 3. In an embodiment, responsively to the output of π-BG 20, demodulation circuit 22 outputs demodulated optical pulses (i.e., intensity modulated) to EORC 24, which responsively transmits, to processor 48, respective raw voltage electrical signals, such as $I_s$ and $I_f$ shown in inset 215, which are indicative of the US waves impinged on π-BG 20. Processor 48 processes the raw signals to derive an US indicative signal, given in a physical unit of Hertz, seen in inset 225, which is directly indicative of the US wave, for such purposes as generating an US image. The signals in insets 215 and 225 are brought by way of example and should not be assumed as being related both to each other (i.e., resulting from the same US wave).

Optical Passive-Demodulation Pulse Interferometry for Ultrasound Detection with High Dynamic Range FIG. 3 is a block diagram that schematically illustrates details elements of the detection apparatus appearing in FIG. 2, in accordance with an embodiment of the present invention. As seen, the output of π-BG 20 is connected to a 50/50 coupler 321 of an MZI 32 of OPDI circuit 22 whose polarization maintaining arms 323 and 325 are coupled to a second coupler 327. In an embodiment, a 45-degree offset exists between the principle axes of arms 323 and 325 of MZI 32.

Accordingly, in the inputs to coupler 327, both the slow and fast polarizations of polarization maintaining arms are excited with equal intensities. The two outputs of MZI 32 (i.e., outputs of coupler 327) are further split into their respective polarization modes by two polarization beam splitters, PBS 341 and PBS 343, respectively, which realize a 2×4 optical hybrid 34.

The four outputs of optical hybrid 34 (O1, O2, O3, and O4) are connected to EORC 24. Balanced photodetectors 421 and 423, included in EORC 24, each measure the difference in optical intensity for a specific polarization mode. The EORC then transmits resulting electronic signals $I_s$ and $I_f$ to processor 48, for further processing as described in FIG. 4.

In an embodiment, the measured electrical signals $I_s$ and $I_f$ are given by:

$$\begin{cases} I_s \cong I_0 \sin\left(\frac{2\pi \Delta n_{avg} \Delta v}{c} + \varphi_0\right) \\ I_f \cong I_0 \cos\left(\frac{2\pi \Delta n_{avg} \Delta v}{c} + \varphi_0\right) \end{cases} \quad \text{Eq. 1}$$

A detailed derivation of signals $I_s$ and $I_f$ is provided in Provisional Patent Application 62/555,066, cited above, whose disclosure is incorporated herein by reference. In eq. 1, $I_0=|E_0|^2$ is the optical pulse intensity, and $$\varphi_0 = \frac{2\pi \Delta n_{avg} v_0}{0}$$

is the phase difference induced between arms 321 and 321 of MZI 32. Since the MZI arms 321 and 323 are weakly birefringent, Eq. 1 is derived assuming the approximation $\Delta n \ll n_{avg}$, where $n_{avg}=(n_s+n_f)/2$ and $\Delta n=(n_s-n_f)$, and where $n_s$ and $n_f$ are the refractive indices of arms 323 and 325 of MZI 32, respectively.

In addition, it is assumed that the ultrasound-induced temporal variations in v is small relative to the carrier frequency, i.e., $\Delta v(t) \ll v_0$, where $v=v_0+\Delta v(t)$.

In an embodiment, the lengths of arm 321 and 323 of MZI 32 are adjusted to create a quarter wavelength difference between the optical path difference of the two polarization arms. The disclosed optical hybrid is implemented, for example, with planar waveguides patterned on a substrate, which are utilized to create an approximate 90-degree phase difference between the two polarizations. In some embodiments of the present invention, the disclosed 90-degree optical hybrid is implemented with a variety of multimode interference (MMI) couplers. For example, in an embodiment, the 90-degree hybrid is implemented using two MZIs with a $$\frac{\lambda}{4} + m \cdot \frac{\lambda}{2}$$

(λ=c/v and m being an integer) length difference between their optical path differences. In another embodiment, the 90-degree hybrid is implemented with a 4×4 MMI.

Figure 4:
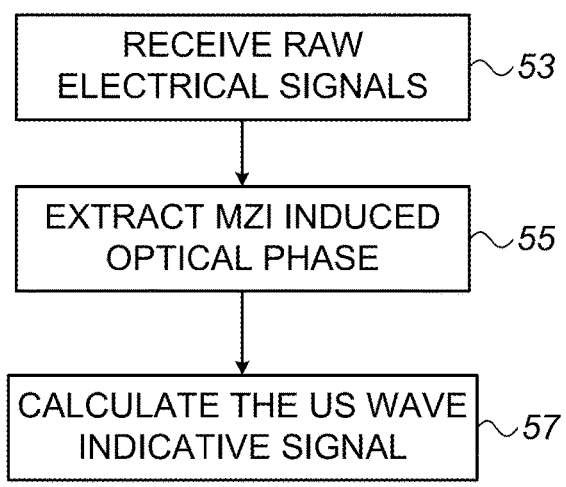
FIG. 4 is a flow-chart that schematically illustrates a method for optical detection of ultrasound, in accordance with an embodiment of the present invention.

FIG. 4 is a flow-chart that schematically illustrates a method for optical detection of a US wave, in accordance with an embodiment of the present invention. The process begins at a receiving raw electrical signals step 53, such as receiving signals $I_s$ and $I_f$, or an associated form of signals $\tilde{I}_s$ and $\tilde{I}_f$, in processor 48. An example of an associated version of Eq. 1 occurs when the measurements are AC-coupled and are given by $\tilde{I}_s=I_s-\sin(\varphi_0)$, and $\tilde{I}_f=I_f-\cos(\varphi_0)$.

Next, at a phase extraction step 55, processor 48 performs a calculation to extract optical phase $\varphi_0$ that MZI 32 induces, as described in detail in the above cited Provisional Patent Application 62/555,066, whose disclosure is incorporated herein by reference. Next, in a modulation frequency calculation step 57, processor 48 calculates, from the associated version of Eq. 1, a processed signal that is indicative of the wave, such as that shown in inset 225 of FIG. 3 above.

Figure 5A:
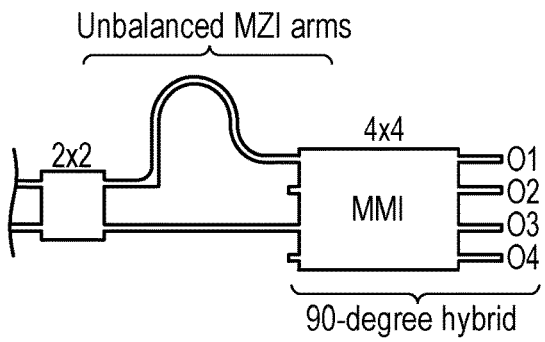
FIGS. 5A and 5B are block diagrams that schematically illustrate PIC-based optical passive-demodulation interferometry (OPDI) circuits, in accordance with additional embodiments of the present invention.
Figure 5B:
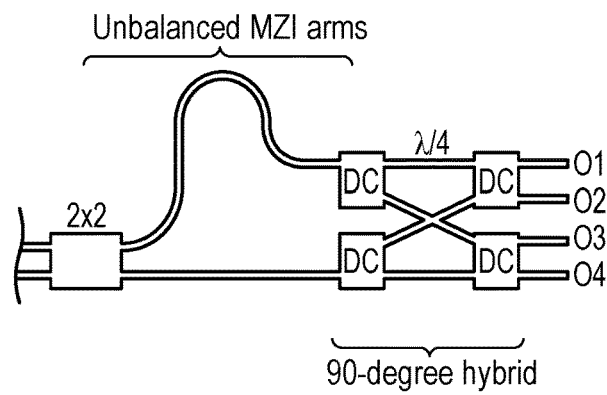

FIGS. 5A and 5B are block diagrams that schematically illustrate PIC-based OPDI circuits, in accordance with additional embodiments of the present invention. Each of these PIC-based OPDI circuits can be used for implementing measurement elements 220 shown in FIGS. 1-3.

FIG. 5A shows a multimode interference (MMI) coupler implementation of a 2×4 MMI 90-degree hybrid using a 4×4 MMI 90-degree hybrid. MMIs are robust against fabrication errors and temperature fluctuations. Alternatively, as FIG. 5B shows, the 90-degree hybrid may be implemented by two MZIs with a λ/4+m·λ/2 (m being an integer) length difference between the optical path difference of the two MZIs.

The 2×2 elements in the input of both schemes, as well as the directional couplers (DCs) in FIG. 7B, may be implemented via 2×2 MMI couplers, or couplers based on evanescent-wave coupling. The optical resonator, such as π-BG 20, can be connected to either of the inputs of the 2×2 MMI coupler.

The unbalanced MZI and the 90-degree hybrid may be fabricated in a planar geometry with 2D waveguides, i.e., waveguides in which the mode in confined in two dimensions and propagated in the third. Such planar designs may be implemented by numerous fabrication techniques for photonic integrated circuits. In particular, silicon photonics, glass waveguides, and polymer waveguides may be used in the implementation.

In general, a passive-modulation scheme enables feeding a signal from an optical resonator, such as a π-BG, to an unbalanced MZI having several outputs, where the phase difference between the outputs of the MZI is different than 180 degrees.

A phase difference of 90 degrees leads to simple implementation, as well as a simple demodulation algorithm. MMIs, then, represent a practical method for implementing 90 degree-hybrids that are scalable (many MMIs can be produced in a single chip) and reproducible (the performance of the MMIs does not change between manufacturing batches). MMIs are also highly versatile and can be used to implement hybrids with various angle differences. While such implementations may not be as simple as the one embodied above with 90-degree hybrid 34, the advantages of MMIs make them a feasible solution.

Figure 6A:
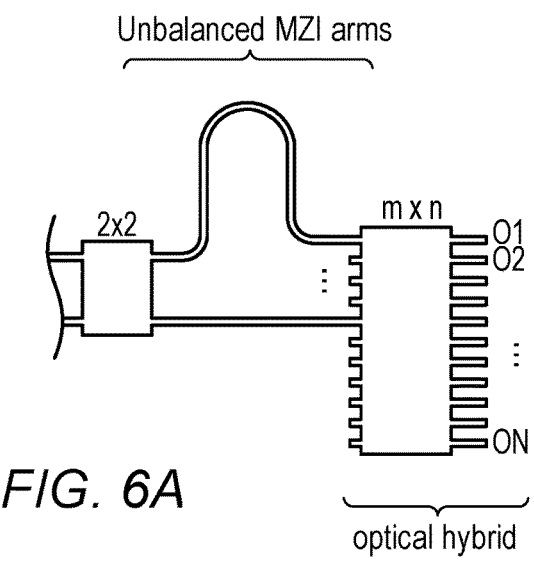
FIGS. 6A and 6B are block diagrams that schematically illustrate PIC-based OPDI circuits, in accordance with other embodiments of the present invention.
Figure 6B:
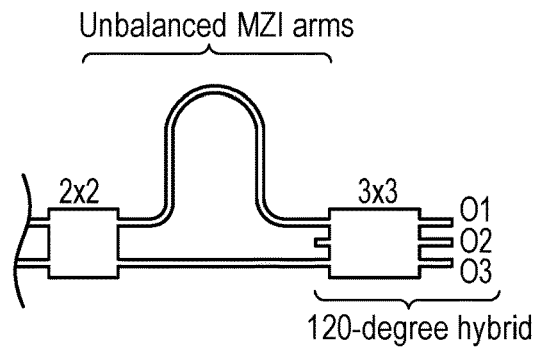

FIGS. 6A and 6B are block diagrams that schematically illustrate PIC-based OPDI circuits, in accordance with other embodiments of the present invention. Each of these PIC-based OPDI circuits can be used for implementing measurement elements 220 shown in FIGS. 1-3.

FIG. 6A demonstrates a general pulse-interferometry demodulation scheme in which an unbalanced two-arm interferometer is connected to an m×n MMI (m and n being integers) that acts as an optical hybrid. An example of a 120-degree optical hybrid implemented by a 3×3 MMI coupler is given in FIG. 6B. The 2×2 elements in the input of both schemes shown in FIGS. 6A and 6B may be implemented via 2×2 MMI couplers or couplers based on evanescent-wave coupling. With the embodiments exemplified by FIGS. 6A and 6B, the electro-optical readout circuitry and demodulation process also differ from that exemplified in FIG. 3 for a 90-degree implementation.

The optical passive-demodulation circuits shown above are depicted purely for the sake of conceptual clarity. In alternative embodiments, any other suitable configuration can be used.

Ultrasound Detection in Thermoacoustic Systems

Figure 7:
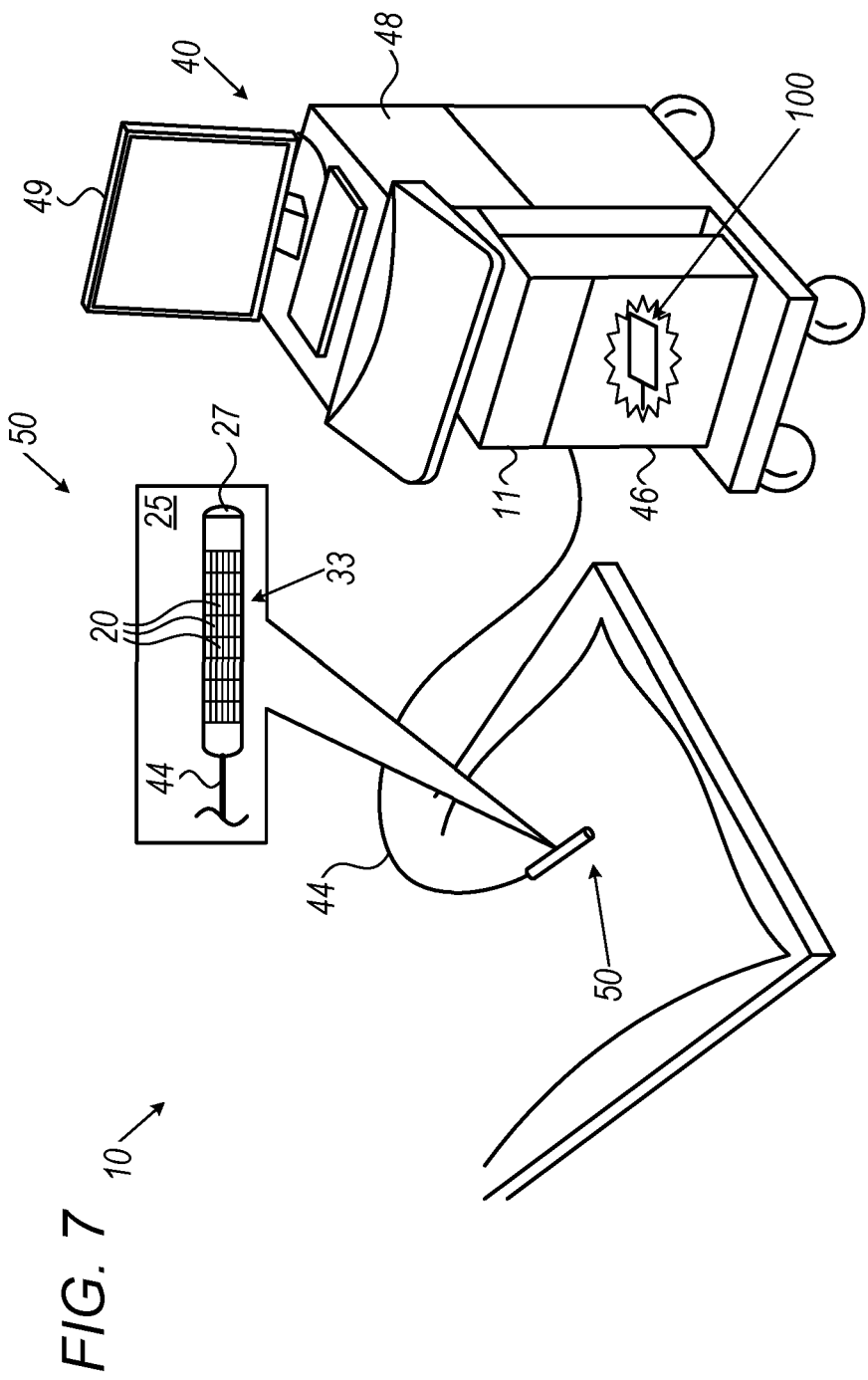
FIG. 7 is a schematic, pictorial illustration of a minimally invasive medical optoacoustic diagnostic system, in accordance with an embodiment of the present invention.

FIG. 7 is a schematic, pictorial illustration of a PIC-based minimally invasive medical optoacoustic diagnostic system 10, in accordance with an embodiment of the present invention. US diagnostic system 10, comprises US console 40 that comprises an interface 46 to which US probe 50 is connected by cable 44. Console 40 further comprises system processor 48.

An interface 46 of system 10 is configured to pass electrical power, through cable 44, to a source 27 of pulsed electromagnetic radiation, which is included in probe 50 and seen in inset 25. Probe 50 is configured for insertion into a cavity of an organ of a patient, and source 27 is configured to, responsively to the driving power from interface 46, generate electromagnetic radiation that upon being absorbed by tissue of organ, heats tissue to generate US waves in an effect known as "thermoacoustic". The effect known as "optoacoustic" is a special case of the thermoacoustic effect, in which modulated light (from visible to infrared) is used to excite US waves.

A pulsed optical source 11 in console 40 supplies, through an optical fiber included in cable 44, optical pulses to PIC-based US detector array 33 comprised in probe 50 (as seen in inset 25). Detector array 33 comprises multiple OR 20, arranged in pixels, each of which is configured to optically detect the resulting opto-acoustically generated US waves using the optical pulses, as described above. Array 33 transmits the optical pulses to PIC-based OPDI array 100, again using an optical fiber included in cable 44, that were frequency modulated in response to the impinging US waves for demodulation and electrical readout of the resulting intensity modulated optical pulses.

The resulting electrical signals are received processor 48 via cable 44 and interface 46. Processor 48 is configured to generate from the measured electrical signals an indicative information, such as an US image, and to display it on a monitor 49.

Typically, processor 48 comprises a general-purpose computer, which is programmed in software to carry out the functions described herein.

The configuration of optical source 27 and array 33 are depicted by way of example. In an embodiment, source 27 is located in console 40 and an optical fiber transmits US exciting optical pulses generated in the console to probe 50. As another example, in another embodiment, the US exciting pulse may be applied outside the body, and only the detection of the resulting US waves is performed by probe 50.

As noted above, US detector array 33 of probe 50 is configured to optically detect the resulting US waves using the disclosed detection method that is based on optical passive-demodulation pulse interferometry, as described below. System 10 can detect US wave that are an order of magnitude weaker (i.e., of lower sound pressure) than alternative solutions. At the same time, system 10 can detect high intensity US waves, and achieve a dynamic range that may exceed 60 dB. Thus, US detector array 33 may enable US system 10 to, for example, spatially resolve anatomical features that are unresolvable by US imaging systems employing piezoelectric US detectors. System 10 could therefore provide US images having a superior image quality.

As noted above, in alternative embodiments, array 33 of OR and/or an array of EORC are implemented using other technologies than PIC. For example, OR and/or EORC arrays are implemented using fiber optics and/or free-space electrooptical devices, such as commercially available packaged π-BG and photodiodes coupled using free-space lenslet arrays.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus for optical detection of ultrasound (US), the apparatus comprising:
a first array of optical resonators (OR), implemented in at least one photonic integrated circuit (PIC) and configured to modulate respective carrier frequencies of optical pulses indicative of US waves impinging thereon;
a second array of optical passive- demodulation interferometers (OPDI), implemented in the at least one PIC, wherein each OPDI is configured to demodulate the optical signal output by the respective OR, so as to generate a respective intensity-modulated optical signal, the OPDI comprising an interferometer having imbalanced arms that are recombined using an optical hybrid;
a third array of respective electro- optical readout circuits (EORC), wherein each EORC is configured to measure the intensity demodulated optical signal produced by the respective OPDI, and to output a respective electrical signal.

2. The apparatus according to claim 1, wherein the third array of EORC are implemented in the at least one PIC.

3. The apparatus according to claim 2, wherein the second array of OPDI and the third array of EORC are implemented on a single PIC.

4. The apparatus according to claim 3, wherein the first array of the OR is implemented on the single PIC together with the second array of OPDI and the third array of EORC.

5. The apparatus according to claim 1, and comprising a processor, which is configured to derive, from respective electrical signals output by the third array of EORC, an output indicative of the impinging US wave.

6. The apparatus according to claim 1, wherein the first array of OR comprise π-phase shifted Bragg gratings.

7. The apparatus according to claim 1, wherein the optical hybrid comprises a 90-degree optical hybrid.

8. The apparatus according to claim 1, wherein the interferometer is configured to generate a predefined optical phase shift between the imbalanced arms, at the carrier frequency.

9. A method for optically detecting ultrasound (US) waves, the method comprising:
using a first array of optical resonators (OR), implemented in at least one photonic integrated circuit (PIC), modulating respective carrier frequencies of optical pulses indicative of US waves impinging thereon;
using a second array of optical passive- demodulation interferometers (OPDI), implemented in the at least one PIC, demodulating the optical signals so as to generate respective intensity-modulated optical signals, wherein each of the OPDIs comprises an interferometer having imbalanced arms that are recombined using an optical hybrid; and
using a third array of electro-optical readout circuits (EORC), measuring the intensity demodulated optical signals and outputting respective electrical signals.

10. The method according to claim 9, wherein the third array of EORC are implemented in the at least one PIC.

11. The method according to claim 10, wherein the second array of OPDI and the third array of EORC are implemented on a single PIC.

12. The method according to claim 11, wherein the first array of the OR is implemented on the single PIC together with the second array of OPDI and the third array of EORC.

13. The method according to claim 9, and comprising deriving, from respective electrical signals output by the third array of EORC, an output indicative of the impinging US wave.

14. The method according to claim 9, wherein the first array of OR comprise π-phase shifted Bragg gratings.

15. The method according to claim 9, wherein the optical hybrid comprises a 90-degree optical hybrid.

16. The method according to claim 9, wherein demodulating the optical signals comprises generating, by the interferometer, a predefined optical phase shift between the imbalanced arms at the carrier frequency.

17. The apparatus according to claim 1, wherein the first array of OR is implemented on a first PIC, and the second array of OPDI is implemented on a second PIC, which is connected to the first PIC by an optical fiber.

18. The apparatus according to claim 17, wherein the first PIC comprises first planar waveguides and a first coupler, which couple the optical signals output by the first array of OR into the optical fiber, and wherein the second PIC comprises second planar waveguides, which couple the optical signals from the optical fiber into the second array of OPDI.

* * * * *